United States Patent
Chen et al.

(10) Patent No.: US 12,296,192 B2
(45) Date of Patent: May 13, 2025

(54) RADIOTHERAPY SYSTEM AND TREATMENT PLAN GENERATION METHOD THEREFOR

(71) Applicant: NEUBORON THERAPY SYSTEM LTD., Fujian (CN)

(72) Inventors: Jiang Chen, Fujian (CN); Wei-Iin Chen, Fujian (CN)

(73) Assignee: NEUBORON THERAPY SYSTEM LTD., Fujian (CN)

( * ) Notice: Subject to any disclaimer, the term of this patent is extended or adjusted under 35 U.S.C. 154(b) by 155 days.

(21) Appl. No.: 18/078,226

(22) Filed: Dec. 9, 2022

(65) Prior Publication Data

US 2023/0111230 A1    Apr. 13, 2023

Related U.S. Application Data

(63) Continuation of application No. PCT/CN2021/097627, filed on Jun. 1, 2021.

(30) Foreign Application Priority Data

Jun. 11, 2020    (CN) .......................... 202010528551.0

(51) Int. Cl.
*A61N 5/10*    (2006.01)

(52) U.S. Cl.
CPC ......... *A61N 5/1031* (2013.01); *A61N 5/1067* (2013.01); *A61N 5/1071* (2013.01); *A61N 2005/1034* (2013.01); *A61N 2005/109* (2013.01)

(58) Field of Classification Search
CPC .. A61N 5/1031; A61N 5/1067; A61N 5/1071; A61N 2005/1034; A61N 2005/109
See application file for complete search history.

(56) References Cited

U.S. PATENT DOCUMENTS 12,064,645 B2 *  8/2024  Ropo ................... A61N 5/1081
2002/0106054 A1   8/2002  Caflisch et al.
(Continued)

FOREIGN PATENT DOCUMENTS

CN    106687177 A    5/2017
CN    110740783 A    1/2020
(Continued)

OTHER PUBLICATIONS

Gong, Taiqian et al., Esophageal Squamous Cell Carcinoma Diagnosis and Treatment, Beijing:Science and Technology Literature Press, 2016.
(Continued)

*Primary Examiner* — Dani Fox
*Assistant Examiner* — Fani Polyzos Boosalis
(74) *Attorney, Agent, or Firm* — Troutman Pepper Locke LLP; Tim Tingkang Xia, Esq.

(57) ABSTRACT

Disclosed are a radiotherapy system and a treatment plan generation method therefor. The radiotherapy system includes a beam irradiation device, a treatment planning module and a control module. The beam irradiation device generates a beam for treatment and irradiates same to a body to be irradiated to form an irradiated site, the treatment planning module generates a treatment plan on the basis of parameters of the beam for treatment and medical image data of the irradiated site, and the control module retrieves a treatment plan corresponding to said body from the treatment planning module and controls the beam irradiation device to sequentially irradiate said body according to at
(Continued)

least two irradiation angles determined according to the treatment plan generation method and the irradiation time corresponding to each irradiation angle.

20 Claims, 3 Drawing Sheets

(56) References Cited

U.S. PATENT DOCUMENTS

| | | |
|---|---|---|
| 2003/0219098 A1 | 11/2003 | McNutt et al. |
| 2005/0197564 A1* | 9/2005 | Dempsey ............ G01R 33/381 378/65 |
| 2007/0086569 A1 | 4/2007 | Johnsen |
| 2009/0050819 A1 | 2/2009 | Ma et al. |
| 2011/0091014 A1 | 4/2011 | Siljamaki et al. |
| 2012/0020460 A1 | 1/2012 | Witten et al. |
| 2012/0165652 A1* | 6/2012 | Dempsey ............ A61N 5/1045 600/410 |
| 2013/0090549 A1 | 4/2013 | Meltsner et al. |
| 2017/0028221 A1 | 2/2017 | Kontaxis et al. |
| 2018/0369611 A1 | 12/2018 | Owens et al. |

FOREIGN PATENT DOCUMENTS

| | | |
|---|---|---|
| CN | 107292075 B | 6/2020 |
| JP | 2019170612 A | 10/2019 |
| JP | WO2020111085 A1 | 10/2021 |
| TW | I647657 B | 1/2019 |
| WO | 2019094824 A1 | 5/2019 |

OTHER PUBLICATIONS

Joshua Wilde et al., Constrained Optimization, Math Camp, 2013.
International Search Report of PCT/CN2021/097627, Aug. 26, 2021.
Chaomin Chen, Study on Three-Dimensional Static Intensity Modulated Radiotherapy, non-official translation: "China Doctoral Dissertations Full-Text Database, Medicine and Health Sciences", 2010, pp. 5-8 & 58.
Chunyu Wang, The dosimetric effect of the angle change after electron beam irradiation for the patients after breast surgery, Chinese Master's Theses Full-text Database, Medicine and Health Sciences, 2016.
Sun Yan, Advanced course in Clinical Oncology, 2017.
R. Barquero et al., Monte Carlo simulation estimates of neutron doses to critical organs of a patient undergoing 18 MV x-ray LINAC-based radiotherapy, 2005.

* cited by examiner

RADIOTHERAPY SYSTEM AND TREATMENT PLAN GENERATION METHOD THEREFOR

CROSS-REFERENCE TO RELATED PATENT APPLICATION

This application is a continuation application of International Application No. PCT/CN2021/097627, filed on Jun. 1, 2021, which claims priority to Chinese Patent Application No. 202010528551.0, filed on Jun. 11, 2020, the disclosures of which are hereby incorporated by reference.

TECHNICAL FIELD

The invention relates to a radiotherapy system and a method for generating a treatment plan, and in particular to a method for generating a treatment plan of a radiotherapy system.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

With the development of atomics, radio therapy, such as cobalt sixty, a linear accelerator, an electron beam, or the like, has become one of the major means to treat cancers. However, traditional photon or electron therapy is restricted by physical conditions of radioactive rays themselves, and thus will also harm a large number of normal tissues on a beam path while killing tumor cells. Furthermore, owing to different levels of sensitivity of tumor cells to radioactive rays, traditional radiotherapy usually has poor treatment effect on malignant tumors (for example, glioblastoma multiforme and melanoma) with radio resistance.

In order to reduce radiation injury to normal tissues around tumors, a target therapy concept in chemotherapy is applied to radiotherapy. With respect to tumor cells with high radio resistance, irradiation sources with high relative biological effectiveness (RBE), such as proton therapy, heavy particle therapy, neutron capture therapy, or the like, are also developed actively now. Here neutron capture therapy combines the abovementioned two concepts, for example, boron neutron capture therapy (BNCT), and provides a better cancer treatment choice than traditional radioactive rays, by specific aggregation of boron-containing drugs in tumor cells in combination with precise beam regulation and control.

BNCT produces two heavily charged particles $^4$He and $^7$Li by using a characteristic of a boron ($^{10}$B)-containing drug having a high capture section for a thermal neutron, and through $^{10}$B (n, $\alpha$)$^7$Li neutron capture and a nuclear fission reaction, and the two particles have a total range approximately equivalent to a cell size, so that radiation injury to an organism may be limited to a cell level. When boron-containing drugs are selectively aggregated in tumor cells, a purpose of locally killing tumor cells may be achieved with an appropriate neutron radioactive source, on premise of not inducing too large injury to normal tissues.

Radiotherapy uses high-energy radiation to destroy tumor cells and prevent the tumor cells from growth and division, under normal tissue and organ-acceptable radiation irradiation tolerance or recoverable slight side-effects, so as to control or cure tumors. Therefore, tumor dose is limited by normal tissue and organ-acceptable radiation dose. Furthermore, benefit of BNCT depends on distribution and accumulation of the boron-containing drug and neutron concentration in the tumor. The distribution and accumulation of the boron-containing drug is affected by tumor characteristics and ability of a patient' metabolism and absorption, and at present, a patient suitable for BNCT is screened through a positron emission tomography (PET) scan. Flux of the neutron is reduced along with the increase of depth in the patient's body, and is inhibited due to interaction with the boron element in the drug, resulting in little neutron concentration in the tumor at a deep position along an incidence direction of the neutron.

A three-dimensional (3D) model is widely applied to the field of analysis and simulation of scientific experiments. For example, in the field of nuclear radiation and protection, in order to simulate absorption dose of a human body under a certain radiation condition to help a doctor to formulate a treatment plan, a computer technology is usually required to perform various processing on medical imaging data, so as to establish an accurate lattice model required by Monte Carlo software, and simulation and calculation are carried out in combination with Monte Carlo software. In an existing neutron capture therapy planning system, irradiation angles are evaluated to select an optimal angle to irradiate a neutron beam, on one hand, radiation dose is required to be increased due to little neutron concentration at a deep position of the tumor, on the other hand, radiation dose is required to be controlled due to limitation of normal tissue and organ-acceptable radiation dose, so that treatment effect is greatly reduced.

Therefore, it is necessary to provide a radiotherapy system and a method for generating a treatment plan of a radiotherapy system.

SUMMARY

In order to overcome defects of the related art, one aspect of the invention provides a radiotherapy system, including a beam irradiation device, a treatment plan module and a control module. The beam irradiation device generates a treatment beam and irradiates the treatment beam to a to-be-irradiated body to form an irradiated site. The treatment plan module generates, according to parameters of the treatment beam generated by the beam irradiation device and medical image data of the irradiated site, a treatment plan determining at least two irradiation angles and irradiation time corresponding to each of the irradiation angles, here the irradiation angle is defined as a vector direction from an irradiation point of the treatment beam to a preset point on a lesion tissue of the irradiated site. The control module retrieves, from the treatment plan module, the treatment plan corresponding to the to-be-irradiated body, and controls the beam irradiation device to irradiate the to-be-irradiated body sequentially according to the at least two irradiation angles determined by the treatment plan and the irradiation time corresponding to each of the irradiation angles. According to distribution of lesion tissues, multiple irradiation angles are used for radiotherapy, so that amount of radiation in a shallow part of the irradiated site is dispersed and reduced, radiation dose accepted by normal tissues and a maximum dose for normal tissues are reduced, and then probability of side-effect occurred to normal tissues after accepting radiotherapy is reduced. Furthermore, the total radiation dose may be properly increased to increase dose for the lesion tissue, especially amount of radiation in a deep part of the lesion tissue, and a minimum dose for the lesion tissue is increased. Multiple incidence directions may also make dose within the lesion tissue more uniform.

Further, the treatment plan module may simulate, through a Monte Carlo simulation program, distribution of radiation dose when the irradiated site is irradiated by the treatment beam, and generate the treatment plan in combination with a mathematical algorithm. Further, the treatment plan module may establish an objective function of a region of interest (ROI) according to the simulated distribution of radiation dose, and perform optimization solution on the objective function to calculate the at least two irradiation angles and the irradiation time corresponding to each of the irradiation angles.

Preferably, the treatment plan module may establish a 3D voxel prosthesis tissue model according to the medical image data of the irradiated site, input the parameters of the treatment beam and the 3D voxel prosthesis tissue model into the Monte Carlo simulation program to simulate sampling of different irradiation angles, and calculate radiation dose $D_{ki}$ of each voxel unit i in unit time at a sampled irradiation angle k.

Preferably, the 3D voxel prosthesis tissue model may have information on tissue type and tissue density, and more accurately, provide tissue type, element composition and density, so that the established geometric model is better matched with an actual situation reflected by the medical image data. Further, the radiotherapy system may be a BNCT system, and the 3D voxel prosthesis tissue model may also have information on tissue boron concentration, so that concentration of the boron-containing drug in each tissue may be clearly known, and an actual situation may be reflected more truly when BNCT irradiation simulation is performed.

Preferably, sampled beam angles may also be screened during sampling of different irradiation angles or after sampling calculation.

Further, the objective function may be expressed by formula 1:

$$F(d_i) = \sum_{i \in N} (d_i - d_i^p)^2 \quad \text{(formula 1)}$$

where $d_i$ is a total dose of voxel i, and $d_i^p$ is a prescription dose of voxel the total dose $d_i$ of voxel i may be calculated by formula 2:

$$d_i = \sum_{k=1}^{n} w_k \cdot D_{ki} \quad \text{(formula 2)}$$

where $w_k$ is irradiation time at different irradiation angles, $D_{ki}$ is a dose of voxel i in unit time at the irradiation angle k, and $d_i$ is the total dose of voxel the prescription dose $d_i^p$ of voxel i may be calculated by formula 3:

$$d_i^p = \frac{d^{pN}}{C_N} \quad \text{(formula 3)}$$

where $d^{pN}$ is a prescription dose of a ROI N, and $C_N$ is the number of voxels of the ROI.

Further, the treatment plan module may use an optimization algorithm to perform optimization solution on the objective function by formula 4:

$$\min\{F(d_i)\} \quad \text{(formula 4)},$$

a design variable of formula 4 is defined as X, here the design variable X is expressed by formula 5:

$$X = \{w_1, w_2 \ldots w_k\} \quad \text{(formula 5)},$$

the at least two irradiation angles k and irradiation time $w_k$ corresponding to different irradiation angles k are determined according to optimal solution of the design variable X. Preferably, the optimization algorithm is a support vector machine (SVM), a response surface method (RSM) or a least square vector regression (LSVR).

Further, the treatment plan module may establish a constraint condition for optimization solution of the objective function. Further, the constraint condition selects one or more normal organs or tissues M, so that a sum $d_M$ of total doses $d_i$ of all voxels i in each of the normal organs or tissues M satisfies formula 6:

$$g(d_M) < 0 \quad \text{(formula 6)}.$$

Preferably, unit of each of the dose, the total dose and the prescription dose in formula 1 to formula 6 is eq-Gy, and unit of the irradiation time is s.

Further preferably, the treatment plan module may evaluate or prefer results of optimization solution of the objective function through dose inspection.

Another aspect of the invention provides a radiotherapy system, including a beam irradiation device, a treatment plan module and a control module. The beam irradiation device generates a treatment beam and irradiates the treatment beam to a to-be-irradiated body to form an irradiated site. The treatment plan module generates, according to parameters of the treatment beam generated by the beam irradiation device and medical image data of the irradiated site, a treatment plan determining multiple irradiation angles and a planned irradiation dose corresponding to each of the irradiation angles, here the irradiation angle is defined as a vector direction from an irradiation point of the treatment beam to a preset point on a lesion tissue of the irradiated site. The control module retrieves, from the treatment plan module, the treatment plan corresponding to the to-be-irradiated body, and controls the beam irradiation device to irradiate the to-be-irradiated body sequentially according to the multiple irradiation angles and the planned irradiation dose corresponding to each of the irradiation angles, during an irradiation treatment of the to-be-irradiated body according to the treatment plan. According to distribution of lesion tissues, multiple irradiation angles are used for radiotherapy, so that amount of radiation in a shallow part of the irradiated site is dispersed and reduced, radiation dose accepted by normal tissues and a maximum dose for normal tissues are reduced, and then probability of side-effect occurred to normal tissues after accepting radiotherapy is reduced. Furthermore, the total radiation dose may be properly increased to increase dose for the lesion tissue, especially amount of radiation in a deep part of the lesion tissue, and a minimum dose for the lesion tissue is increased. Multiple incidence directions may also make dose within the lesion tissue more uniform.

Still another aspect of the invention provides a method for generating a treatment plan, including the following operations. A 3D voxel prosthesis tissue model is established according to medical image data. Parameters of a beam are defined in a Monte Carlo simulation program, sampling of different irradiation angles is simulated, and radiation dose $D_{ki}$ of each voxel unit i in unit time at a sampled irradiation angle k is calculated. An objective function of a ROI is established, and optimization solution is performed on the objective function to calculate at least two irradiation angles and irradiation time corresponding to each of the irradiation angles, here the irradiation angle is defined as a vector direction from an irradiation point of the beam to a preset point on a lesion tissue of the 3D voxel prosthesis tissue model. Multiple irradiation angles are used for radiotherapy, so that amount of radiation in a shallow part of the irradiated site is dispersed and reduced, radiation dose accepted by normal tissues and a maximum dose for normal tissues are reduced, and then probability of side-effect occurred to normal tissues after accepting radiotherapy is reduced. Furthermore, the total radiation dose may be properly increased to increase dose for the lesion tissue, especially amount of radiation in a deep part of the lesion tissue, and a minimum dose for the lesion tissue is increased. Multiple incidence directions may also make dose within the lesion tissue more uniform.

Preferably, the objective function may be expressed by formula 1:

$$F(d_i) = \sum_{i \in N} (d_i - d_i^p)^2 \quad \text{(formula 1)}$$

where $d_i$ is a total dose of voxel i, and $d_i^p$ is a prescription dose of voxel i, the total dose $d_i$ of voxel i may be calculated by formula 2:

$$d_i = \sum_{k=1}^{n} w_k \cdot D_{ki} \quad \text{(formula 2)}$$

where $w_k$ is irradiation time at different irradiation angles, $D_{ki}$ is a dose of voxel i in unit time at the irradiation angle k, and $d_i$ is the total dose of voxel i, the prescription dose $d_i^p$ of voxel i may be calculated by formula 3:

$$d_i^p = \frac{d^{pN}}{C_N} \quad \text{(formula 3)}$$

where $d^{pN}$ is a prescription dose of a ROI N, and $C_N$ is the number of voxels of the ROI.

Further, an optimization algorithm may be used to perform optimization solution on the objective function by formula 4:

$$\min\{F(d_i)\} \quad \text{(formula 4)},$$

a design variable of formula 4 is defined as X, here the design variable X is expressed by formula 5:

$$X = \{w_1, w_2 \ldots w_k\} \quad \text{(formula 5)},$$

the at least two irradiation angles k and irradiation time $w_k$ corresponding to different irradiation angles k are determined according to optimal solution of the design variable X. Further preferably, the optimization algorithm is SVM, RSM or LSVR.

Further, the method for generating a treatment plan may further include the following operations. A constraint condition is established for optimization solution of the objective function. Further preferably, the constraint condition selects one or more normal organs or tissues M, so that a sum $d_M$ of total doses $d_i$ of all voxels i in each of the normal organs or tissues M satisfies formula 6:

$$g(d_M) < 0 \quad \text{(formula 6)}.$$

Preferably, unit of each of the dose, the total dose and the prescription dose in formula 1 to formula 6 is eq-Gy, and unit of the irradiation time is s.

Preferably, the method for generating a treatment plan may further include an operation of dose inspection, and results of optimization solution of the objective function are evaluated or preferred through the dose inspection.

Preferably, the operation of establishing the 3D voxel prosthesis tissue model according to medical image data may further include the following operations. The medical image data is read. A 3D medical image voxel model is established. A boundary of the ROI is defined or read. A tissue type (element composition) and tissue density of each voxel unit is defined. The 3D voxel prosthesis tissue model is established. The 3D voxel prosthesis tissue model is established according to a conversion relationship among the medical image data, the tissue type and the tissue density, and more accurately, provides tissue type (element composition) and tissue density, so that the established geometric model is better matched with an actual situation reflected by the medical image data. Further, the method for generating a treatment plan may be applied to BNCT, and the operation of establishing the 3D voxel prosthesis tissue model according to medical image data may further include the following operations. A tissue boron concentration in each voxel unit is defined, so that concentration of the boron-containing drug in each tissue may be clearly known, and an actual situation may be reflected more truly when BNCT irradiation simulation is performed.

Preferably, sampled beam angles may also be screened during sampling of different irradiation angles or after sampling calculation.

According to the radiotherapy system and the method for generating a treatment plan, amount of radiation in a shallow part of the irradiated site may be dispersed and amount of radiation in a deep part of the lesion tissue may be increased, to reduce a maximum dose for normal tissues and increase a minimum dose for the lesion tissue, and to ensure uniform distribution of dose within the lesion tissue.

BRIEF DESCRIPTION OF THE DRAWINGS

The accompanying drawings illustrate one or more embodiments of the disclosure and together with the written description, serve to explain the principles of the disclosure. Wherever possible, the same reference numbers are used throughout the drawings to refer to the same or like elements of an embodiment.

DETAILED DESCRIPTION OF THE DISCLOSURE

Embodiments of the invention will be further described in detail below with reference to the drawings, to enable those skilled in the art to implement the embodiments according to text of the description.

Preferably, a neutron capture therapy system and a method for generating a treatment plan thereof are taken as the embodiments of the invention. Neutron capture therapy, especially BNCT, will be briefly described below.

Application of neutron capture therapy as an effective means for cancer treatment gradually increases in recent years, in which BNCT is most commonly seen, and neutrons supplied to BNCT may be supplied by a nuclear reactor or accelerator. The embodiments of the invention take an accelerator BNCT as an example, and basic components of the accelerator BNCT generally include an accelerator for accelerating charged particles (such as protons, deuterium cores, or the like), a target, a thermal removal system and a beam shaping body, here the accelerated charged particles act with the metal target to generate neutrons, and an appropriate nuclear reaction may be selected according to characteristics such as a desired neutron yield and energy, available energies of the accelerated charged particles, a current, physical and chemical properties of the metal target, or the like. Nuclear reactions as commonly discussed include $^7Li(p, n)\ ^7BE$ and $^9Be(p, n)\ ^9B$, both of which are endothermic reactions and have energy thresholds of 1.881 MeV and 2.055 MeV respectively. An ideal neutron source for BNCT is a epithermal neutron at a keV energy level, then theoretically, when protons with energies only slightly higher than the threshold are used to bombard a metallic lithium target, neutrons with relatively low energies may be generated for clinical application without too much retarding treatment. However, proton action cross sections of lithium (Li) and beryllium (Be) metallic targets with the threshold energy are not high, therefore protons with higher energies are usually selected to initiate a nuclear reaction, to generate a large enough neutron flux.

Figure 1:
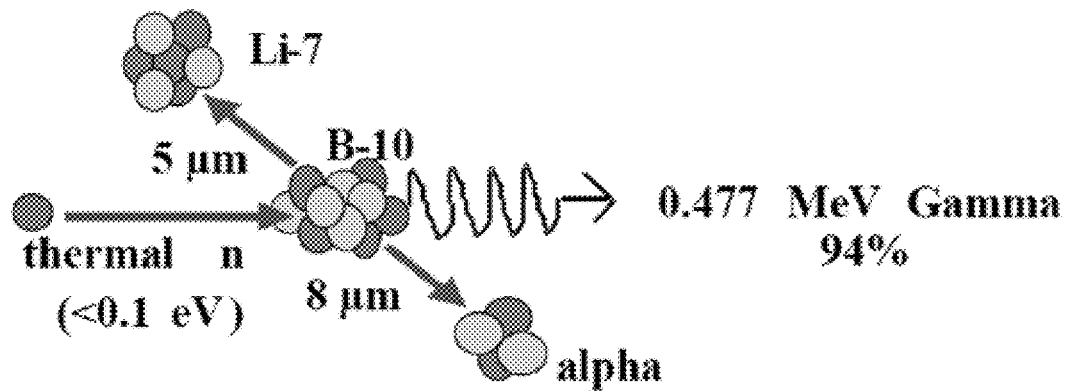
FIG. 1 is a schematic diagram of a boron neutron capture reaction.
Figure 2:
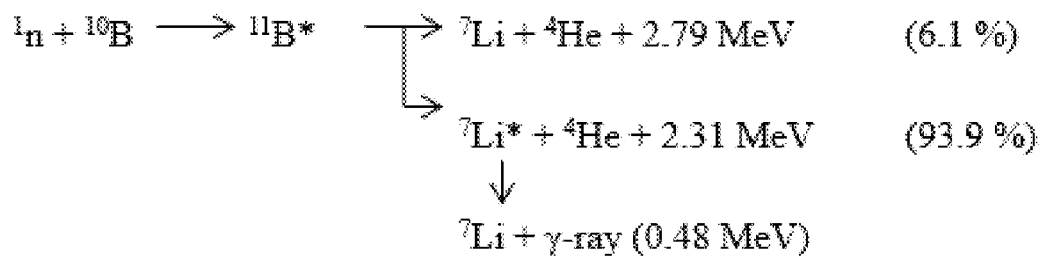
FIG. 2 is an equation of a $^{10}B(n, \alpha)\,^{7}Li$ neutron capture nuclear reaction.

BNCT produces two heavily charged particles $^4He$ and $^7Li$ by using a characteristic of a boron ($^{10}B$)-containing drug having a high capture section for a thermal neutron, and through $^{10}B(n, \alpha)\ ^7Li$ neutron capture and a nuclear fission reaction. Referring to FIGS. 1 and 2, a schematic diagram of a boron neutron capture reaction, and an equation of a $^{10}B$ (n, α) $^7Li$ neutron capture nuclear reaction are shown respectively, and the two charged particles have an average energy of about 2.33 MeV, and have characteristics of high linear energy transfer (LET) and short range. LET and range of α particle are 150 keV/μm and 8 μm respectively, LET and range of the heavily charged particle $^7Li$ are 175 keV/μm and 5 μm respectively, and the two particles have a total range approximately equivalent to a cell size, so that radiation injury to an organism may be limited to a cell level. When boron-containing drugs are selectively aggregated in tumor cells, a purpose of locally killing tumor cells may be achieved with an appropriate neutron radioactive source, on premise of not inducing too large injury to normal tissues.

Figure 3:
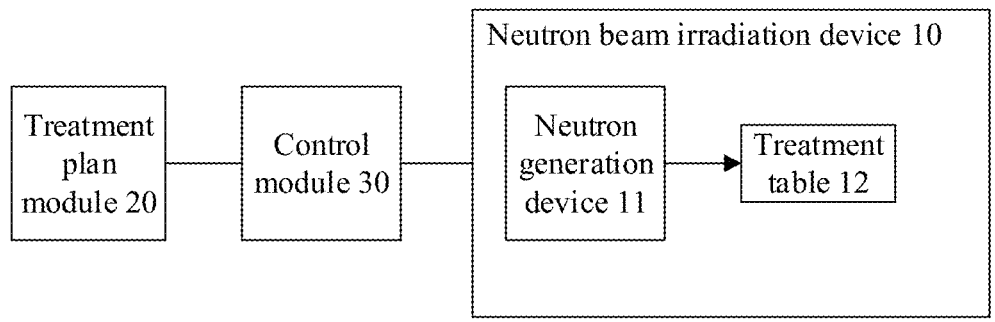
FIG. 3 is a block diagram of a neutron capture therapy system according to an embodiment of the invention.

Referring to FIG. 3, the radiotherapy system according to an embodiment is preferably a neutron capture therapy system 100, including a neutron beam irradiation device 10, a treatment plan module 20 and a control module 30. The neutron beam irradiation device 10 includes a neutron generation device 11 and a treatment table 12, and the neutron generation device 11 generates a treatment neutron beam and irradiates the treatment neutron beam to a patient on the treatment table 12 to form an irradiated site. In neutron capture therapy, in order to simulate absorption dose of an organism under a certain radiation condition to help a doctor to formulate a treatment plan, a computer technology is usually required to perform various processing on medical imaging, so as to establish an accurate lattice model required by Monte Carlo software, and simulation and calculation are carried out in combination with Monte Carlo software. The treatment plan module 20 simulates distribution of radiation dose during irradiation treatment on the patient through a Monte Carlo simulation program, according to parameters of the neutron beam generated by the neutron generation device 11 and medical image data of the patient's irradiated site, and generates the treatment plan in combination with a mathematical algorithm. In an embodiment, the treatment plan module 20 may establish an objective function of a ROI according to the simulated distribution of radiation dose, and perform optimization solution on the objective function to calculate at least two irradiation angles and irradiation time corresponding to each of the irradiation angles. It may be understood that at least two irradiation angles and irradiation time corresponding to each of the irradiation angles may also be calculated by other methods. The control module 30 retrieves, from the treatment plan module 20, a treatment plan corresponding to a current patient, and controls irradiation of the neutron beam irradiation device 10 according to the treatment plan, for example, control the neutron generation device 11 to generate neutrons and irradiate the patient on the treatment table 12 sequentially according to the at least two irradiation angles determined by the treatment plan and the irradiation time corresponding to each of the irradiation angles, or the like. It may be understood that the irradiation time corresponding to each of the irradiation angles may also be a planned irradiation dose corresponding to each of the irradiation angles, and may be obtained by simulated calculation and transformation.

Figure 4:
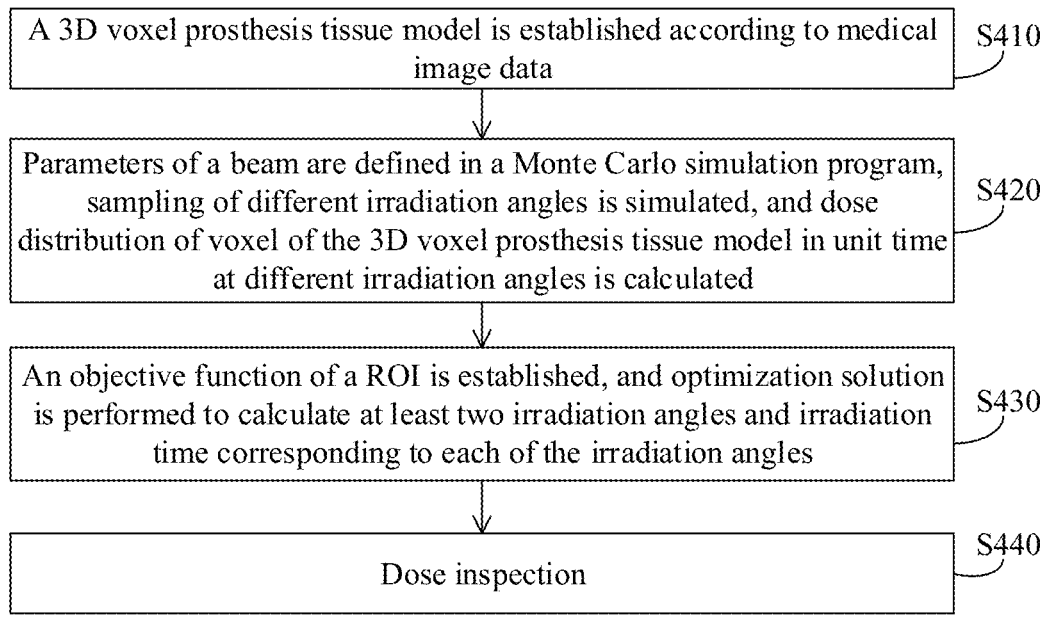
FIG. 4 is a flowchart of a method for generating a treatment plan by a treatment plan module according to an embodiment of the invention.

Referring to FIG. 4, a method for generating a treatment plan by the treatment plan module 20 according to an embodiment includes the following operations.

In operation S410, a 3D voxel prosthesis tissue model is established according to medical image data.

In operation S420, parameters of a beam are defined in a Monte Carlo simulation program (such as Monte Carlo N Particle Transport Code (MCNP)), sampling of different irradiation angles k is simulated, and dose distribution $D_{ki}$ of voxel i of the 3D voxel prosthesis tissue model in unit time at different irradiation angles k is calculated.

In operation S430, an objective function of a ROI is established, and optimization solution is performed to calculate at least two irradiation angles and irradiation time corresponding to each of the irradiation angles. The ROI may be a key organ, such as an eye, a liver, or the like; or, may be an important tissue, such as bone tissue, brain tissue, or the like; or, may be a tumor cell.

In operation S440, dose inspection is performed, evaluate or prefer results of optimization solution of the objective function.

Figure 5:
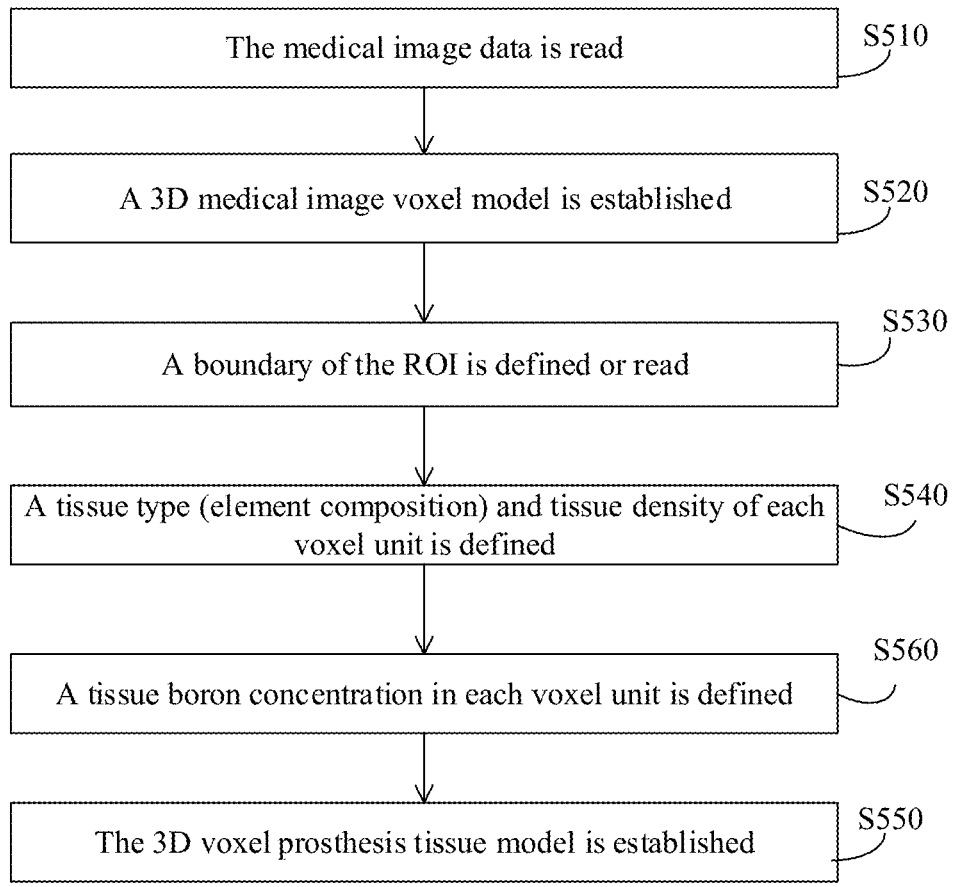
FIG. 5 is a flowchart of a method for establishing a 3D voxel prosthesis tissue model according to an embodiment of the invention.

Referring to FIG. 5, in an embodiment, the operation S410 of establishing the 3D voxel prosthesis tissue model according to medical image data may further include the following operations.

In operation S510, the medical image data is read.

In operation S520, a 3D medical image voxel model is established.

In operation S530, a boundary of the ROI is defined or read.

In operation S540, a tissue type (element composition) and tissue density of each voxel unit is defined, and may be defined automatically according to a conversion relationship among computed tomography (CT) image data, the tissue type and the tissue density, or may be manually defined by a user, for example, a specific tissue type and tissue density is given for a voxel unit within a boundary of each ROI.

In operation S550, the 3D voxel prosthesis tissue model is established.

The 3D voxel prosthesis tissue model is established according to a conversion relationship among the medical image data, the tissue type and the tissue density, and more accurately, provides tissue type (element composition) and tissue density, so that the established geometric model is better matched with an actual situation reflected by the medical image data. When the radiotherapy system is a BNCT system, the operation S410 of establishing the 3D voxel prosthesis tissue model according to medical image data may further include an operation S560 after the operation S540. In operation S560, a tissue boron concentration in each voxel unit is defined. It may be understood that the operation S560 may also occurs prior to the operation S540. It may be clearly known from a geometric model marked with information of the tissue boron concentration that concentration of the boron-containing drug in each tissue, and then an actual situation may be reflected more truly when neutron irradiation simulation is performed.

A detailed process of establishing the 3D voxel prosthesis tissue model according to the medical image data may refer to a patent application disclosed on Mar. 8, 2017 with a publication number CN 106474634A, and entitled "METHOD FOR ESTABLISHING GEOMETRIC MODEL BASED ON MEDICAL IMAGE DATA", which is incorporated here in its entirety.

At present, Monte Carlo method is a tool capable of accurately simulating collision trajectories and energy distribution of nuclear particles in 3D space within an irradiation target, and a human body model is combined with the Monte Carlo simulation program, so that absorption dose of the human body in a radiation environment may be calculated and evaluated accurately. In the operation S420, parameters (such as beam energy, intensity, radius, or the like) of a beam are defined in the Monte Carlo simulation program, different irradiation angles are sampled, to simulatively calculate dose distribution of the 3D voxel prosthesis tissue model at different irradiation angles, that is, to simulatively calculate irradiation dose n $D_{ki}$ of each voxel unit i in unit time at the sampled irradiation angle k under irradiation of the defined beam respectively.

During sampling, it is required to determine a starting position and beam angle of calculating the beam. During calculation, the starting position and angle may be determined by a forward algorithm or a backward algorithm. In the forward algorithm, the starting position is determined in an in-vitro position and may be sampled and calculated sequentially according to a fixed angle or distance interval, or may also be performed in a random sampling manner; a part of the beam angle may be set as a vector direction from an irradiation point to centroid of a tumor or a deepest position of the tumor, and a specific endpoint position of the tumor may be adjusted according to user requirements. In the backward algorithm, the starting position is determined to be in a range of the tumor, the starting position may be centroid of the tumor, the deepest position or a random point in the range of the tumor, and the beam angle may be taken by using random sampling or sampling according to a specified interval.

During sampling, beam angles may also be screened, for example, beam angles are evaluated, and beam angles for subsequent calculation are selected according to result of evaluation; or beam angles are screened after sampling calculation, for example, screening is performed according to result of distribution of radiation dose or result of evaluation of beam angles. A method for evaluating the beam angle will not be described in detail here, and may refer to a patent application disclosed on Jun. 16, 2017 with a publication number $C_N$ 106853272A, and entitled "METHOD FOR EVALUATING IRRADIATION ANGLE OF BEAM", which is incorporated here in its entirety.

Figure 6:
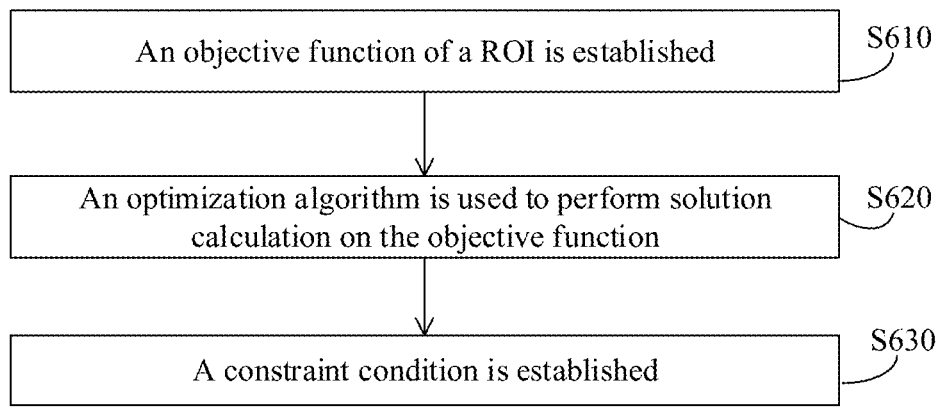
FIG. 6 is a flowchart of a method for establishing an objective function of a ROI and calculating through optimization solution according to an embodiment of the invention.

Referring to FIG. 6, the operation S430 of establishing the objective function of ROI, and performing optimization solution to calculate the at least two irradiation angles and the irradiation time corresponding to each of the irradiation angles, is described in detail below. In an embodiment, this operation may further include the following operations.

In operation S610, an objective function of a ROI N (it is a tumor cell in the embodiment) is established for the ROI N. In an embodiment, the objective function is a square of a difference between a desired dose (prescription dose) and a calculated dose, to uniformly distribute doses of all voxels in the ROI N, and it may be understood that other objective functions may also be used. In the embodiment, the objective function may be expressed by formula 1:

$$F(d_i) = \sum_{i \in N}(d_i - d_i^p)^2 \qquad \text{(formula 1)}$$

where $d_i$ is a total dose of voxel i, and $d_i^p$ is a prescription dose of voxel i.

The total dose $d_i$ of voxel i may be calculated by formula 2:

$$d_i = \sum_{k=1}^{n} w_k \cdot D_{ki} \qquad \text{(formula 2)}$$

where $w_k$ is irradiation time at different irradiation angles, $D_{ki}$ is a dose of voxel i in unit time at the irradiation angle k, and $d_i$ is the total dose of voxel i.

The prescription dose $d_i^p$ of voxel i may be calculated by formula 3:

$$d_i^p = \frac{d^{pN}}{C_N} \qquad \text{(formula 3)}$$

where $d^{pN}$ is a prescription dose of the ROI N, and $C_N$ is the number of voxels of the ROI. The prescription dose $d^{pN}$ of the ROI N is usually given by a physician after synthetic judgment according to a patient's conditions.

In operation S620, an optimization algorithm is used to perform optimization solution on the objective function by formula 4, so that distribution difference between the desired dose and the calculated dose is reduced as much as possible:

$$\min\{F(d_1)\} \quad \text{(formula 4)},$$

a design variable of formula 4 is defined as X, here the design variable X is expressed by formula 5:

$$X=\{w_1, w_2 \ldots w_k\} \quad \text{(formula 5)}.$$

An appropriate optimization algorithm, such as SVM, RSM, LSVR, or the like is used, so that optimal solution of the design variable X may be obtained, and multiple irradiation angles k and irradiation time $w_k$ corresponding to different irradiation angles k may be determined based on the obtained optimal solution. It may be understood that optimization solution of the objective function may also be performed by other ways.

In operation S630, a constraint condition is established, so that optimization solution of the objective function meets treatment requirements better. In the embodiment, dose limit value of a normal organ or tissue is taken as the constraint condition, one or more normal organs or tissues M are selected, so that a sum $d_M$ of total doses $d_i$ of all voxels i in each of the normal organs or tissues M satisfies formula 6:

$$g(d_M)<0 \quad \text{(formula 6)}.$$

It may be understood that a constraint condition may not be established, or, different constraint conditions may also be established, to obtain different optimal solutions to form different treatment plan schemes for an operator such as a physician to select.

After optimization solution of the objective function, results of optimization solution of the objective function are evaluated or preferred through the operation S440 of dose inspection. For example, a dose volume histogram (DVH) is used to evaluate superposed dose distribution obtained by multiple irradiation angles k determined by optimal solution of the design variable X and irradiation time $w_k$ corresponding to different irradiation angles k upon simulating in the 3D voxel prosthesis tissue model; and evaluation may also be performed on evaluation of irradiation angles as described above. Different optimal solutions obtained based on different constraint conditions may also be evaluated simultaneously, so that an operator such as a physician selects a treatment plan scheme which meets requirements better. It may be understood that dose inspection may not be performed, either.

According to distribution of tumors, multiple irradiation angles are used for radiotherapy, so that amount of neutrons in a shallow part of the patient's irradiated site is dispersed and reduced, radiation dose accepted by normal tissues and a maximum dose for normal tissues are reduced, and then probability of side-effect occurred to normal tissues after accepting radiotherapy is reduced. Furthermore, the total radiation dose may be properly increased to increase dose for the tumor, especially amount of neutrons in a deep part of the tumor, and a minimum dose for the tumor is increased. Multiple incidence directions may also make dose within the tumor more uniform.

Unit of each of the dose, the total dose and the prescription dose in formula 1 to formula 6 is eq-Gy, and unit of the irradiation time is s. It may be understood that some simple transformations, such as simple transformations of doses and time units of formula 1 to formula 6 still fall within the scope of protection of the invention. A total number of irradiation angles K is at least two, a specific number may be manually set, or may be automatically obtained through an algorithm, or may be arc-shaped regulated and controlled continuously, and sampling of the irradiation angle k may be performed on the patient's same side or opposite side.

After the treatment plan module 20 manually selects and determines a treatment plan scheme through calculation and by an operator, the control module 30 retrieves the treatment plan according to instructions, and controls the neutron beam irradiation device 10 to irradiate the patient sequentially according to multiple irradiation angles determined by the treatment plan and irradiation time corresponding to the multiple irradiation angles. It should be understood that a first irradiation angle for irradiating the patient and irradiation time corresponding thereto may be irradiation with a maximum dose applied to the tumor, followed by irradiation at other irradiation angles for supplementary doses, and after irradiation at a current irradiation angle is completed, irradiation is adjusted according to a next irradiation angle. The adjustment of the irradiation angle may be achieved by the control module 30 controlling a direction of a beam outlet of the neutron beam generation device 11 (e.g., a rotatable framework); or, may be achieved by controlling positioning of the patient, here positioning of the patient may be achieved by the control module 30 directly controlling movement of the treatment table 12 according to the treatment plan; or, may be achieved by an operator such as a physician positioning the patient in a simulated positioning chamber (not shown) according to the treatment plan, and then manually or automatically adjusting position of the treatment table 12 and the patient in an irradiation chamber (not shown) according to positioning of the patient determined by the simulated positioning.

It may be understood that the invention may also be applied to other radiotherapy fields which is well known by those skilled in the art and may be simulated by Monte Carlo software, such as proton, heavy ion, X-ray or gamma ray therapy, or the like, and the neutron beam irradiation device is another radiation beam irradiation device; and the invention may also be applied to other diseases which may be treated with irradiation of radioactive rays, such as Alzheimer's disease and rheumatoid arthritis, and tumor cells are other lesion tissues, and the patient may also be another to-be-irradiated body.

While the illustrative specific implementations of the invention has been described as above, so that those skilled in the art understand the invention, it should be clear that the invention is not limited to the scope of the specific implementations, various changes are apparent for those skilled in the art and fall within the scope of protection of the invention, as long as these changes fall within the spirit and scope of the invention as defined and determined by the appended claims.

What is claimed is:

1. A radiotherapy system, characterized in that the radiotherapy system comprises:
   a beam irradiation device generating a treatment beam and irradiating the treatment beam to a to-be-irradiated body to form an irradiated site; and
   a computer including a processor and a storage storing computer executable code, wherein the computer executable code, when executed by the processor, is configured to provide a treatment plan module and a control module;
   the treatment plan module generating, according to parameters of the treatment beam generated by the beam irradiation device and medical image data of the irradiated site, a treatment plan determining at least two irradiation angles and irradiation time corresponding to each of the irradiation angles, wherein the irradiation angle is defined as a vector direction from an irradiation point of the treatment beam to a preset point on a lesion tissue of the irradiated site; and the control module retrieving, from the treatment plan module, the treatment plan corresponding to the to-be-irradiated body, and controlling the beam irradiation device to irradiate the to-be-irradiated body sequentially according to the at least two irradiation angles determined by the treatment plan and the irradiation time corresponding to each of the irradiation angles.

2. The radiotherapy system of claim 1, wherein the treatment plan module simulates, through a Monte Carlo simulation program, distribution of radiation dose when the irradiated site is irradiated by the treatment beam, and generates the treatment plan in combination with a mathematical algorithm.

3. The radiotherapy system of claim 2, wherein the treatment plan module establishes an objective function of a region of interest (ROI) according to the simulated distribution of radiation dose, and perform optimization solution on the objective function to calculate the at least two irradiation angles and the irradiation time corresponding to each of the irradiation angles.

4. The radiotherapy system of claim 3, wherein the treatment plan module establishes a three-dimensional (3D) voxel prosthesis tissue model according to the medical image data of the irradiated site, inputs the parameters of the treatment beam and the 3D voxel prosthesis tissue model into the Monte Carlo simulation program to simulate sampling of different irradiation angles, and calculates radiation dose $D_{ki}$ of each voxel unit i in unit time at a sampled irradiation angle k.

5. The radiotherapy system of claim 4, wherein the radiotherapy system is a boron neutron capture therapy (BNCT) system, and the 3D voxel prosthesis tissue model has information on tissue type, tissue density, and tissue boron concentration.

6. The radiotherapy system of claim 4, wherein the treatment plan module screens sampled beam angles during sampling of different irradiation angles or after sampling calculation.

7. The radiotherapy system of claim 4, wherein the objective function is expressed by formula 1:

$$F(d_i) = \sum_{i \in N}(d_i - d_i^p)^2 \quad \text{(formula 1)}$$

where $d_i$ is a total dose of voxel i, and $d_i^p$ is a prescription dose of voxel i, the total dose $d_i$ of voxel i is calculated by formula 2:

$$d_i = \sum_{k=1}^{n} w_k \cdot D_{ki} \quad \text{(formula 2)}$$

where $w_k$ is irradiation time at different irradiation angles, $D_{ki}$ is a dose of voxel i in unit time at the irradiation angle k, and $d_i$ is the total dose of voxel i, the prescription dose $d_i^p$ of voxel i is calculated by formula 3:

$$d_i^p = \frac{d^{pN}}{C_N} \quad \text{(formula 3)}$$

where $d^{pN}$ is a prescription dose of a ROI N, and $C_N$ is the number of voxels of the ROI.

8. The radiotherapy system of claim 7, wherein the treatment plan module uses an optimization algorithm to perform optimization solution on the objective function by formula 4:

$$\min\{F(d_i)\} \quad \text{(formula 4)},$$

a design variable of formula 4 is defined as X, wherein the design variable X is expressed by formula 5:

$$X = \{w_1, w_2 \ldots w_k\} \quad \text{(formula 5)},$$

the at least two irradiation angles k and irradiation time $w_k$ corresponding to different irradiation angles k are determined according to optimal solution of the design variable X.

9. The radiotherapy system of claim 8, wherein the treatment plan module establishes a constraint condition for optimization solution of the objective function, the constraint condition selects one or more normal organs or tissues M, so that a sum $d_M$ of total doses $d_i$ of all voxels i in each of the normal organs or tissues M satisfies formula 6:

$$g(d_M) < 0 \quad \text{(formula 6)}.$$

10. The radiotherapy system of claim 3, wherein the treatment plan module evaluates or prefers results of optimization solution of the objective function through dose inspection.

11. A method for generating a treatment plan, characterized in that the method comprises steps of:

establishing a three-dimensional (3D) voxel prosthesis tissue model according to medical image data;

defining parameters of a beam in a Monte Carlo simulation program, simulating sampling of different irradiation angles, and calculating radiation dose $D_{ki}$ of each voxel unit i in unit time at a sampled irradiation angle k; and establishing an objective function of a region of interest (ROI), and performing optimization solution on the objective function to calculate at least two irradiation angles and irradiation time corresponding to each of the irradiation angles, wherein the irradiation angle is defined as a vector direction from an irradiation point of the beam to a preset point on a lesion tissue of the 3D voxel prosthesis tissue model.

12. The method for generating a treatment plan of claim 11, wherein the objective function is expressed by formula 1:

$$F(d_i) = \sum_{i \in N}(d_i - d_i^p)^2 \quad \text{(formula 1)}$$

where $d_i$ is a total dose of voxel i, and $d_i^p$ is a prescription dose of voxel i, the total dose $d_i$ of voxel i is calculated by formula 2:

$$d_i = \sum_{k=1}^{n} w_k \cdot D_{ki} \quad \text{(formula 2)}$$

where $w_k$ is irradiation time at different irradiation angles, $D_{ki}$ is a dose of voxel i in unit time at the irradiation angle k, and $d_i$ is the total dose of voxel i, the prescription dose $d_i^p$ of voxel i is calculated by formula 3:

$$d_i^p = \frac{d^{pN}}{C_N} \quad \text{(formula 3)}$$

where $d^{pN}$ is a prescription dose of a ROI N, and $C_N$ is the number of voxels of the ROI.

13. The method for generating a treatment plan of claim 12, wherein an optimization algorithm is used to perform optimization solution on the objective function by formula 4:

$$\min\{F(d_i)\} \quad \text{(formula 4)}$$

a design variable of formula 4 is defined as X, wherein the design variable X is expressed by formula 5:

$$X=\{w_1, w_2 \ldots w_k\} \quad \text{(formula 5)},$$

the at least two irradiation angles k and irradiation time $w_k$ corresponding to different irradiation angles k are determined according to optimal solution of the design variable X.

14. The method for generating a treatment plan of claim 13, further comprising a step of:
establishing a constraint condition for optimization solution of the objective function, the constraint condition selecting one or more normal organs or tissues M, so that a sum $d_M$ of total doses $d_i$ of all voxels i in each of the normal organs or tissues M satisfies formula 6:

$$g(d_M)<0 \quad \text{(formula 6)}.$$

15. The method for generating a treatment plan of claim 13, wherein the optimization algorithm is SVM, RSM or LSVR.

16. The method for generating a treatment plan of claim 13, wherein unit of each of the dose, the total dose and the prescription dose in formula 1 to formula 6 is eq-Gy, and unit of the irradiation time is s.

17. The method for generating a treatment plan of claim 11, further comprising a step of dose inspection, and evaluating or preferring results of optimization solution of the objective function through the dose inspection.

18. The method for generating a treatment plan of claim 11, wherein the operation of establishing the 3D voxel prosthesis tissue model according to medical image data may further include the following operations:
reading the medical image data;
establishing a 3D medical image voxel model is established;
defining or reading a boundary of the ROI;
defining a tissue type and tissue density of each voxel unit is defined;
establishing the 3D voxel prosthesis tissue model.

19. The method for generating a treatment plan of claim 11, wherein the method for generating a treatment plan may be applied to BNCT, and the operation of establishing the 3D voxel prosthesis tissue model according to medical image data may further include defining a tissue boron concentration in each voxel unit.

20. A radiotherapy system, characterized in that the radiotherapy system comprises:
a beam irradiation device generating a treatment beam and irradiating the treatment beam to a to-be-irradiated body to form an irradiated site; and
a computer including a processor and a storage storing computer executable code, wherein the computer executable code, when executed by the processor, is configured to provide a treatment plan module and a control module;
the treatment plan module generating, according to parameters of the treatment beam generated by the beam irradiation device and medical image data of the irradiated site, a treatment plan determining multiple irradiation angles and a planned irradiation dose corresponding to each of the irradiation angles, wherein the irradiation angle is defined as a vector direction from an irradiation point of the treatment beam to a preset point on a lesion tissue of the irradiated site; and
the control module retrieving, from the treatment plan module, the treatment plan corresponding to the to-be-irradiated body, and controlling the beam irradiation device to irradiate the to-be-irradiated body sequentially according to the multiple irradiation angles and the planned irradiation dose corresponding to each of the irradiation angles.

* * * * *